United States Patent
Rupcich et al.

(10) Patent No.: US 11,141,079 B2
(45) Date of Patent: Oct. 12, 2021

(54) SYSTEMS AND METHODS FOR PROFILE-BASED SCANNING

(71) Applicant: General Electric Company, Schenectady, NY (US)

(72) Inventors: Franco Rupcich, Wauwatosa, WI (US); Chelsey Amanda Lewis, Waukesha, WI (US); Christine Carol Hammond, Oconomowoc, WI (US); Dominic Joseph Crotty, Waukesha, WI (US); Mark Vincent Profio, Elm Grove, WI (US)

(73) Assignee: General Electric Company, Schenectady, NY (US)

(*) Notice: Subject to any disclaimer, the term of this patent is extended or adjusted under 35 U.S.C. 154(b) by 180 days.

(21) Appl. No.: 15/882,868

(22) Filed: Jan. 29, 2018

(65) Prior Publication Data

US 2019/0231224 A1 Aug. 1, 2019

(51) Int. Cl.
*G06T 7/00* (2017.01)
*A61B 5/107* (2006.01)
*A61B 6/03* (2006.01)
*G06T 11/00* (2006.01)
*A61B 5/00* (2006.01)
*A61B 5/055* (2006.01)

(52) U.S. Cl.
CPC .......... *A61B 5/1077* (2013.01); *A61B 5/0033* (2013.01); *A61B 5/7264* (2013.01); *A61B 6/032* (2013.01); *G06T 7/97* (2017.01); *G06T 11/003* (2013.01); *A61B 5/055* (2013.01); *G06T 2207/10081* (2013.01)

(58) Field of Classification Search
CPC ..... A61B 5/0033; A61B 5/055; A61B 5/1077; A61B 5/7264; A61B 6/032; A61B 6/488; A61B 6/544; A61B 6/545; G16H 50/20; G06T 11/003; G06T 2207/10081; G06T 7/97

See application file for complete search history.

(56) References Cited

U.S. PATENT DOCUMENTS

| | | | |
|---|---|---|---|
| 6,222,907 B1 | 4/2001 | Gordon, III et al. | |
| 6,345,114 B1* | 2/2002 | Mackie | A61N 5/1048 378/65 |
| 6,636,622 B2* | 10/2003 | Mackie | A61N 5/1048 378/145 |
| 9,173,617 B2 | 11/2015 | Hough et al. | |
| 9,642,589 B2 | 5/2017 | Profio et al. | |
| 2004/0122708 A1* | 6/2004 | Avinash | G16H 10/20 705/2 |
| 2008/0103834 A1* | 5/2008 | Reiner | A61B 6/5294 705/3 |

(Continued)

*Primary Examiner* — Ian L Lemieux

(57) ABSTRACT

Methods and systems are provided for profile-based selection of imaging parameters for a clinical context. In one embodiment, a method comprises selecting a profile based on an indication of clinical context for a scan of a patient, selecting one or more sub-profiles based on the profile, selecting imaging settings for the scan based on the profile and the one or more sub-profiles, and performing the scan according to the selected imaging settings. In this way, a scan prescription may be defined more efficiently and personally for a patient while improving quality assurance and managing an x-ray radiation dose of the patient.

20 Claims, 4 Drawing Sheets

(56) References Cited

U.S. PATENT DOCUMENTS

| | | |
|---|---|---|
| 2012/0148131 A1 | 6/2012 | Couch et al. |
| 2012/0213326 A1* | 8/2012 | Walker .................... G06F 19/00 378/4 |
| 2016/0253443 A1 | 9/2016 | Li et al. |
| 2016/0262714 A1* | 9/2016 | Krauss ................. A61B 5/0064 |
| 2018/0242917 A1* | 8/2018 | Bagherzadeh ......... A61B 6/481 |
| 2018/0289985 A1* | 10/2018 | Kontaxis .............. A61N 5/1047 |
| 2019/0035118 A1* | 1/2019 | Zhao .................... G06T 3/4076 |
| 2019/0099148 A1* | 4/2019 | Rupcich ................... H05G 1/08 |
| 2019/0113587 A1* | 4/2019 | Paulson ............. G01R 33/4808 |
| 2019/0231224 A1* | 8/2019 | Rupcich ................ A61B 6/545 |

\* cited by examiner

SYSTEMS AND METHODS FOR PROFILE-BASED SCANNING

FIELD

Embodiments of the subject matter disclosed herein relate to non-invasive diagnostic imaging, and more particularly, to computed tomography (CT) imaging.

BACKGROUND

In CT imaging, an x-ray source may be rotated around an object of interest (e.g., a patient or an organ of a patient) to obtain imaging information. The object of interest is injected with a contrast agent (e.g., radiocontrast agent, an ionic contrast agent, a barium sulfate contrast agent, and so on) to provide maximum contrast in the imaging information. During a scan, x-rays emitted from the x-ray source and attenuated by the object of interest are collected or detected by a detector and used to reconstruct a diagnostic image.

Acquisition settings correspond to a plurality of user selections defining various mechanical and/or processing actions to acquire and reconstruct the imaging information. The acquisition settings form a scan prescription effecting characteristics of the diagnostic image such as coverage size, spatial resolution, and the like. The acquisition settings are interdependent with one another, requiring the user to adjust numerous acquisition settings to adjust a characteristic of the diagnostic image, such as image noise. Due to the interdependencies, users anecdotally develop groupings of acquisition settings focused on providing machine-specific adjustments. However, the developed groups do not account for variations in patient anatomies, which result in the user manually adjusting the acquisition settings corresponding to trade-offs in dose and image quality. Thus, there is a need for ensuring reliable diagnostic outcomes with consistent image quality of diagnostic images, across patients, using CT imaging.

BRIEF DESCRIPTION

In one embodiment, a method comprises selecting a profile based on an indication of clinical context for a scan of a patient, selecting one or more sub-profiles based on the profile, selecting imaging settings for the scan based on the profile and the one or more sub-profiles, and performing the scan according to the selected imaging settings. In this way, a scan prescription may be defined more efficiently and personally for a patient while improving quality assurance and managing an x-ray radiation dose of the patient.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of CT imaging. In particular, systems and methods are provided for a profile-based selection of imaging parameters for a clinical context. An example of a CT imaging system that may be used to acquire images in accordance with the present techniques is provided in FIGS. 1-2. A plurality of profiles that embed clinical domain knowledge provide automated guidance for the selection of acquisition parameters which may be organized into sub-profiles, as shown in FIG. 3. Methods for profile-based scanning of a patient, such as the methods shown in FIGS. 4-5, may include selecting a profile and one or more sub-profiles based on the clinical context as well as patient attributes, and scanning the patient in accordance with the settings prescribed by the selected profile and sub-profiles.

Though a CT system is described by way of example, it should be understood that the present techniques may also be useful when applied to images acquired using other imaging modalities, such as tomosynthesis, MRI, C-arm angiography, and so forth. The present discussion of a CT imaging modality is provided merely as an example of one suitable imaging modality.

Figure 1:
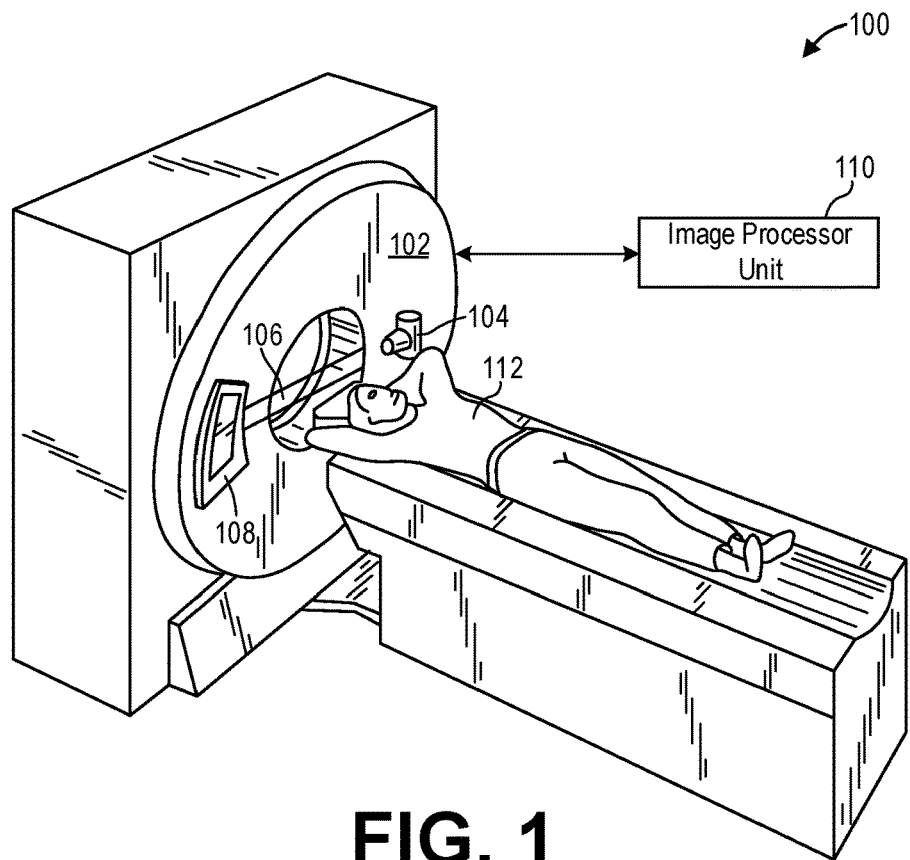
FIG. 1 shows a pictorial view of an imaging system according to an embodiment.

FIG. 1 illustrates an exemplary CT system 100 configured to allow fast and iterative image reconstruction. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray radiation source 104 configured to project a beam of x-ray radiation 106 for use in imaging the subject 112. Specifically, the x-ray radiation source 104 is configured to project the x-rays 106 towards a detector array 108 positioned on the opposite side of the gantry 102. Although FIG. 1 depicts only a single x-ray radiation source 104, in certain embodiments, multiple x-ray radiation sources may be employed to project a plurality of x-rays 106 for acquiring projection data corresponding to the subject 112 at different energy levels.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered backprojection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112.

In some known CT imaging system configurations, a radiation source projects a fan-shaped beam which is collimated to lie within an X-Y plane of a Cartesian coordinate system and generally referred to as an "imaging plane." The radiation beam passes through an object being imaged, such as the patient or subject 112. The beam, after being attenuated by the object, impinges upon an array of radiation detectors. The intensity of the attenuated radiation beam received at the detector array is dependent upon the attenuation of a radiation beam by the object. Each detector element of the array produces a separate electrical signal that is a measurement of the beam attenuation at the detector location. The attenuation measurements from all the detectors are acquired separately to produce a transmission profile.

In some CT systems, the radiation source and the detector array are rotated with a gantry within the imaging plane and around the object to be imaged such that an angle at which the radiation beam intersects the object constantly changes. A group of radiation attenuation measurements, i.e., projection data, from the detector array at one gantry angle is referred to as a "view." A "scan" of the object includes a set of views made at different gantry angles, or view angles, during one revolution of the radiation source and detector. It is contemplated that the benefits of the methods described herein accrue to medical imaging modalities other than CT, so as used herein the term view is not limited to the use as described above with respect to projection data from one gantry angle. The term "view" is used to mean one data acquisition whenever there are multiple data acquisitions from different angles, whether from a CT, PET, or SPECT acquisition, and/or any other modality including modalities yet to be developed as well as combinations thereof in fused embodiments.

In an axial scan, the projection data is processed to reconstruct an image that corresponds to a two-dimensional slice taken through the object. One method for reconstructing an image from a set of projection data is referred to in the art as the filtered backprojection (FBP) technique. Transmission and emission tomography reconstruction techniques also include statistical iterative methods such as maximum likelihood expectation maximization (MLEM) and ordered-subsets expectation reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a helical scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present disclosure in which data representing an image is generated but a viewable image is not. Therefore, as used herein the term "image" broadly refers to both viewable images and data representing a viewable image. However, many embodiments generate (or are configured to generate) at least one viewable image.

Figure 2:
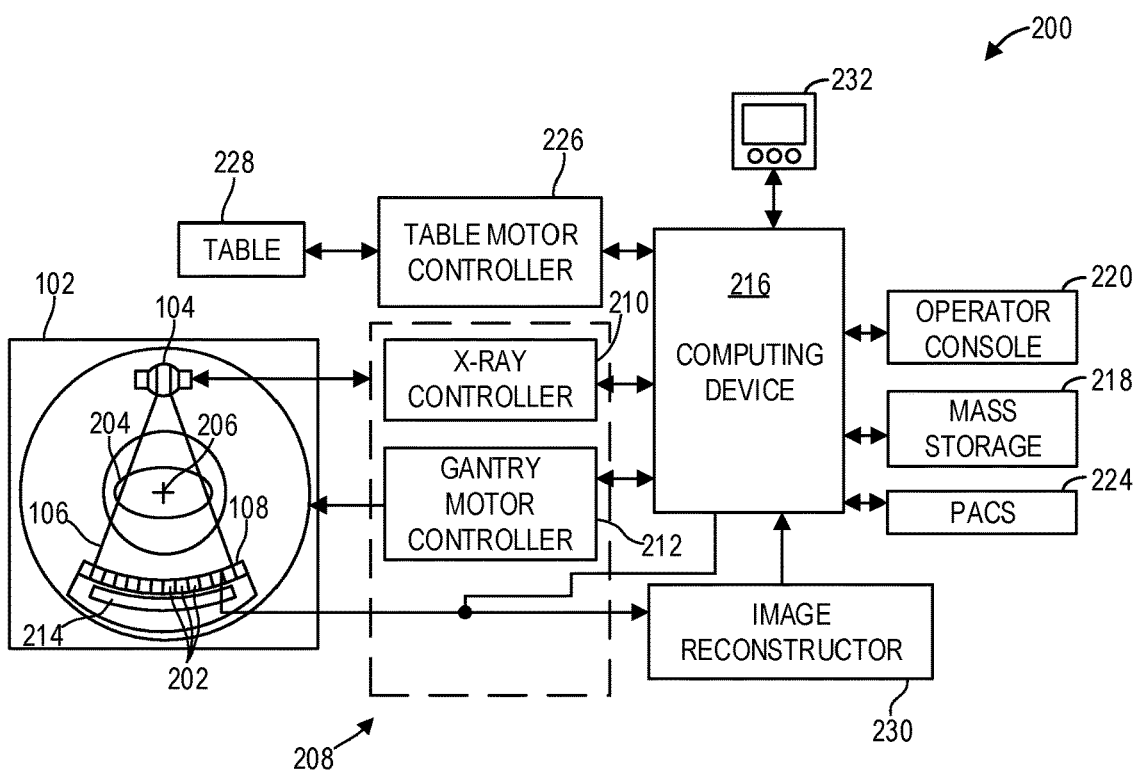
FIG. 2 shows a block schematic diagram of an exemplary imaging system according to an embodiment.
Figure 3:
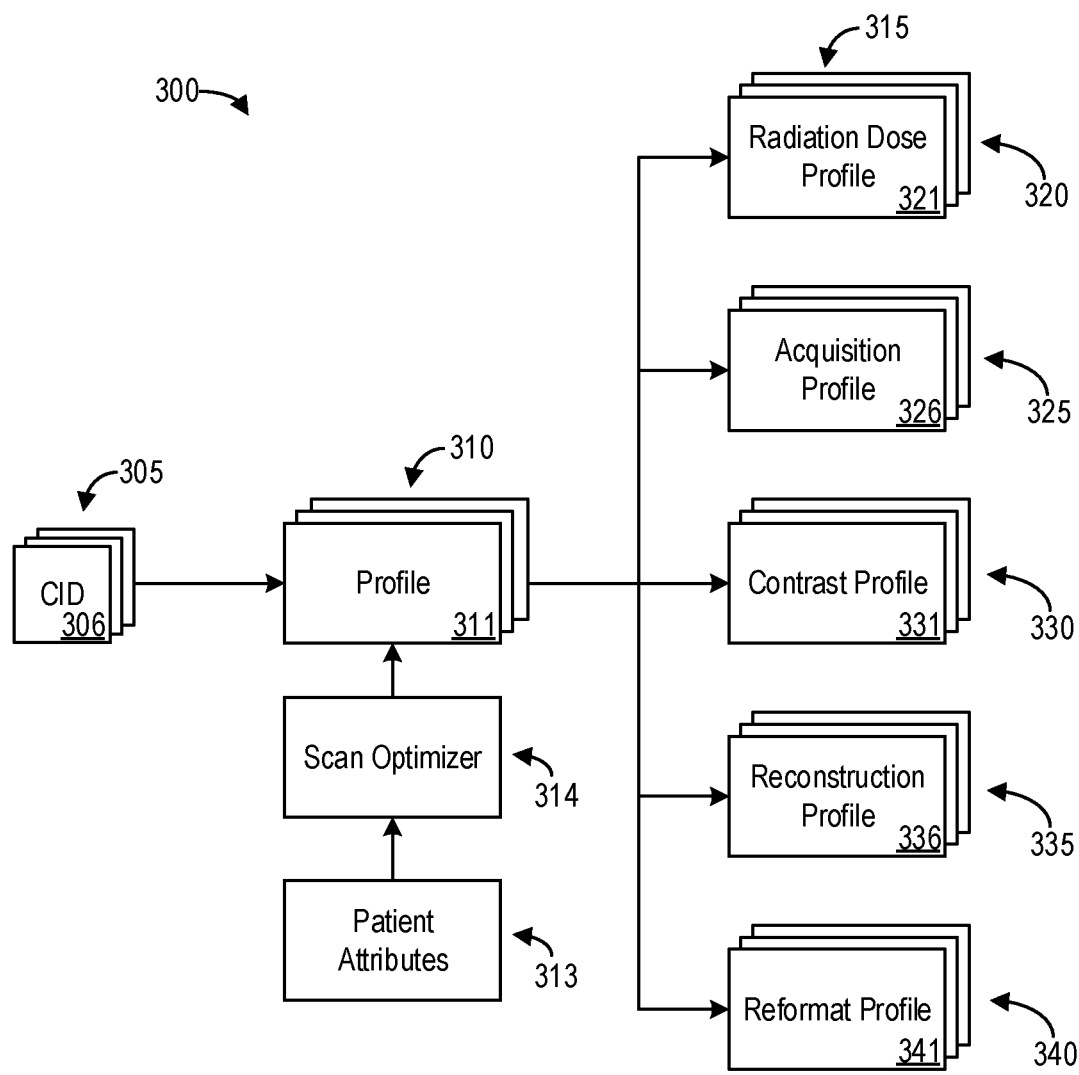
FIG. 3 shows a block diagram illustrating an example profile architecture for guided selection of imaging parameters according to an embodiment.

FIG. 2 illustrates an exemplary imaging system 200 similar to the CT system 100 of FIG. 1. In accordance with aspects of the present disclosure, the imaging system 200 is configured to perform diagnostic scans in accordance with profiles and sub-profiles selected based on the clinical context for the scan as well as attributes of the subject being scanned. In one embodiment, the imaging system 200 includes the detector array 108 (see FIG. 1). The detector array 108 further includes a plurality of detector elements 202 that together sense the x-ray beams 106 (see FIG. 1) that pass through a subject 204 such as a patient to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray radiation source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

The acquired sets of projection data may be reconstructed to form one or more images of the internal anatomy or structure of the subject 204. Once reconstructed, the image produced by the imaging system 200 reveals internal features of the subject 204. In traditional approaches to diagnosis of medical conditions, such as disease states, and more generally of medical events, a radiologist or physician would consider a hard copy or display of the image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray radiation source 104. In certain embodiments, the control mechanism 208 further includes an x-ray controller 210 configured to provide power and timing signals to the x-ray radiation source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computer or computing device 216. In one example, the computing device 216 stores the data in a storage device such as mass storage 218. The mass storage 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) and/or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the imaging system 200 either includes or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 228 which may comprise a motorized table. Particularly, the table motor controller 226 moves the table 228 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more of the functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device or mass storage 218. Alternatively, the image reconstructor 230 transmits the reconstructed images to the computing device 216 for generating useful patient information for diagnosis and evaluation. In certain embodiments, the computing device 216 transmits the reconstructed images and/or the patient information to a display 232 communicatively coupled to the computing device 216 and/or the image reconstructor 230.

The various methods and processes described further herein may be stored as executable instructions in non-transitory memory on a computing device in imaging system 200. For example, image reconstructor 230 may include such executable instructions in non-transitory memory, and may apply the methods described herein to reconstruct an image from scanning data. In another embodiment, computing device 216 may include the instructions in non-transitory memory, and may apply the methods described herein, at least in part, to a reconstructed image after receiving the reconstructed image from image reconstructor 230. In yet another embodiment, the methods and processes described herein may be distributed across image reconstructor 230 and computing system 216.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

FIG. 3 shows a high-level block schematic diagram illustrating an example profile architecture 300 for guided selection of imaging parameters according to an embodiment. As described further herein, the profile architecture 300 enables personalized x-ray and contrast load dosing for a given clinical task. The profile architecture 300 may be implemented in non-transitory memory of a computing device, such as computing device 216 and/or image reconstructor 230.

The profile architecture 300 includes a plurality of clinical identifiers (CIDs) 305, a profile database 310, and a plurality of sub-profile databases 315. A CID of the plurality of CIDs 305, such as CID 306, provides a clinical context having multiple candidate acquisition settings. The CID may include an anatomy of interest and a clinical scan identification. Each CID of the plurality of CIDs 305 is logically mapped to a profile, such as profile 311, of the profile database 310 for selection of clinically relevant prioritization of primary scan or "critical to quality" (CTQ) attributes corresponding to one or more characteristics of the resultant diagnostic image. The scan attributes may include, but are not limited to, a temporal resolution, a material discrimination accuracy, a contrast-to-noise ratio, a coverage size, a spatial resolution, an artifact suppression attribute, and/or the like.

The profile database 310 includes a plurality of profiles such as profile 311. A profile 311 of the profile database 310 models clinical domain knowledge by specifying the prioritization of scan attributes for the given clinical context. In this way, the profiles of the profile database 310 encapsulate clinical domain knowledge.

The plurality of sub-profile databases 315 include a plurality of sub-profiles that prescribe settings for a scan. Different types of settings may be grouped into different sub-profiles. As an illustrative and non-limiting example, the plurality of sub-profile databases 315 includes a radiation dose profile database 320, an acquisition profile database 325, a contrast profile database 330, a reconstruction profile database 335, and a reformat profile database 340.

The radiation dose profile database 320 includes a plurality of radiation dose profiles such as radiation dose profile 321 that prescribe radiation dose settings for a scan. For example, the radiation dose profile 321 may prescribe a tube voltage (e.g., kV level), tube current (e.g., mA), and other settings that impact radiation dose, such as bowtie filter, for a scan.

The acquisition profile database 325 includes a plurality of acquisition profiles such as acquisition profile 326 that prescribe acquisition settings for a scan. For example, the acquisition profile 326 may prescribe gantry rotation speed, focal spot size, scan range, table pitch, helical pitch, collimation, and other settings relating to the acquisition of projection data for a scan.

The contrast profile database 330 includes a plurality of contrast profiles such as contrast profile 331 that prescribe contrast settings for a scan. For example, the contrast profile 331 may prescribe contrast settings such as injection flow rate, contrast volume, injection duration, injection pressure, injection delay, and so on for a scan.

The reconstruction profile database 335 includes a plurality of reconstruction profiles such as reconstruction profile 336 that prescribe reconstruction settings for a scan. For example, the reconstruction profile 336 may prescribe reconstruction settings such as reconstruction kernel, post-processing filters, slice thickness, temporal window, and so on.

The reformat profile database 340 includes a plurality of reformat profiles such as reformat profile 341 that prescribe reformat settings for generating reformatted images for a scan. For example, the reformat profile 341 may prescribe a reconstruction kernel, slice thickness, target image quality, orientation(s), and other reconstruction settings for reformatted images.

Each sub-profile in the plurality of sub-profile databases 315 may be generated from a priori information such as patient population acquisition studies and pre-programmed rule sets. Additionally or alternatively, the sub-profiles of the plurality of sub-profile databases 315 may be generated from user inputs via a user interface such as operator console 220.

Each CID of the plurality of CIDs 305 may be mapped or linked to a corresponding profile of the profile database 310. For example, the CID 306 may be linked to the profile 311. Further, each profile of the profile database 310 may be linked to one or more sub-profiles in each sub-profile database of the plurality of sub-profile databases 315. For example, the profile 311 may be linked to the radiation dose profile 321, the acquisition profile 326, the contrast profile 331, the reconstruction profile 336, and the reformat profile 341. The particular sub-profiles that the profile 311 may be linked to depend on the priorities designated by the profile 311.

Furthermore, the profile 311 may be linked to multiple sub-profiles in sub-profile database. For example, the profile 311 may be linked to multiple radiation dose profiles in the radiation dose profile database 320 as well as multiple contrast profiles in the contrast profile database 330. For a given scan of a patient, patient attributes 313 describing the patient, including but not limited to size (e.g., height and weight), age, heart rate, and medical history, may be used to select which particular sub-profile should be used for the scan. For example, the profile 311 may be linked to a first radiation dose profile, a second radiation dose profile, and a third radiation dose profile of the radiation dose profile database 320 that correspond to appropriate radiation dose settings for different patient sizes. Further, the profile 311 may be linked to a first contrast profile, a second contrast profile, and a third contrast profile of the contrast profile database 330 that correspond to appropriate contrast settings for different combinations of patient age and size. To personalize the scan for a given patient, the appropriate radiation dose profile and/or contrast profile is selected from the plurality of sub-profiles linked to the profile 311 based on the patient attributes 313.

To select an appropriate sub-profile for a given profile, the patient attributes 313 may be input to a scan optimizer 314 that selects one or more sub-profiles in the plurality of sub-profile databases 315 based on the patient attributes 313 and the clinical context indicated by the CID 306. Further, a target level for an image quality metric (e.g., noise index) and/or a dose target (e.g., target CTDIvol and contrast load) may be input, automatically via the profile 311 or user input via operator console 220, to the scan optimizer 314 to aid the selection of the sub-profiles.

Furthermore, it should be appreciated that the sub-profiles of the plurality of sub-profile databases 315 comprise modular building blocks for constructing a scan protocol. Thus, in addition to simplifying the workflow of selecting and adjusting imaging parameters for a scan, the profile architecture 300 enables users to easily create their own profiles for the profile database 310 by combining different combinations of sub-profiles in the plurality of sub-profile databases 315.

Figure 4:
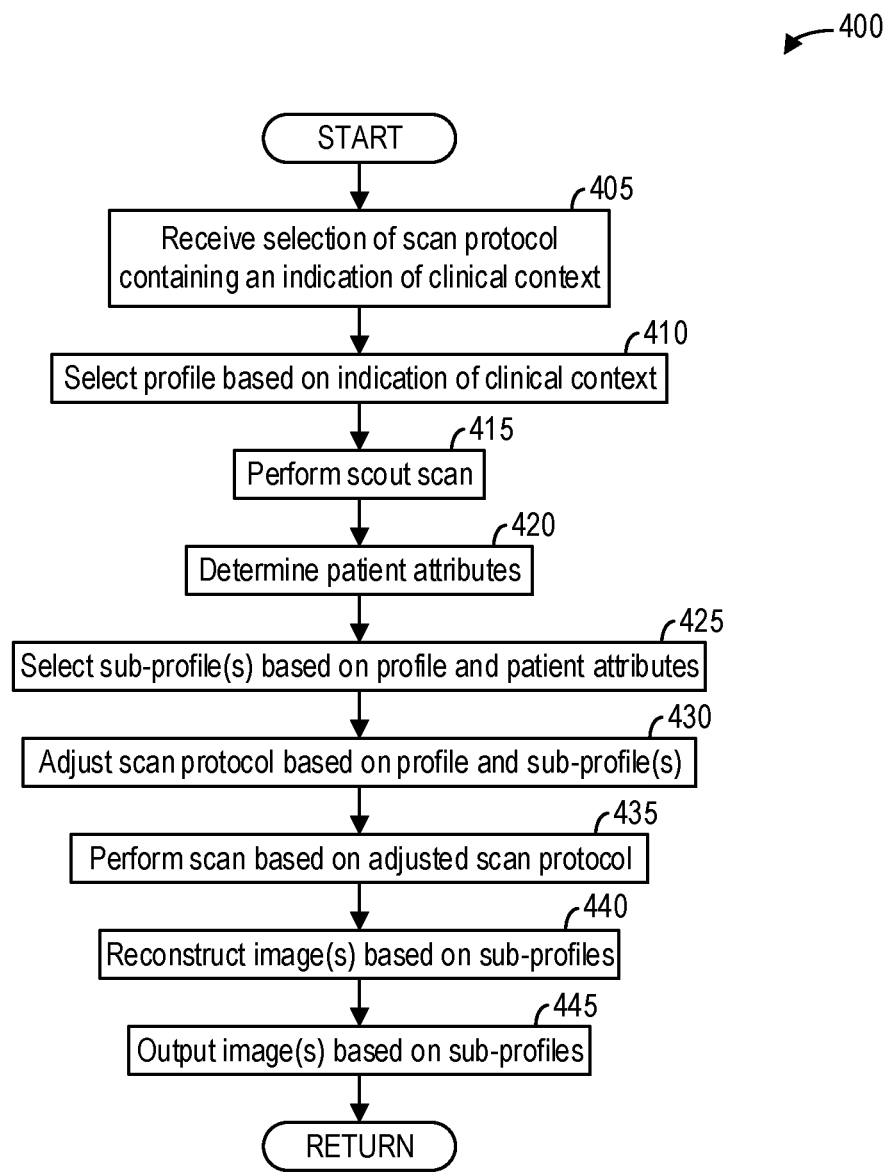
FIG. 4 shows a high-level flow chart illustrating an example method for profile-based scanning according to an embodiment.

FIG. 4 shows a high-level flow chart illustrating an example method 400 for profile-based scanning according to an embodiment. In particular, method 400 relates to a guided selection of imaging settings for an imaging system based on profiles and/or sub-profiles that encapsulate clinical domain knowledge. Method 400 is described with regard to the systems and components of FIGS. 1-3, though it should be appreciated that the method may be implemented with other systems and components without departing from the scope of the present disclosure. Method 400 may be implemented as executable instructions in non-transitory memory of a computing device, such as computing device 216.

Method 400 begins at 405. At 405, method 400 receives a selection of a scan protocol containing an indication of clinical context. For example, a user of the imaging system may select a scan protocol via an operator console, such as operator console 220. Method 400 thus receives the selection of the scan protocol from the operator console. In some examples, the selected scan protocol includes an indication of clinical context, such as a CID.

At 410, method 400 selects a profile based on the indication of clinical context. The profile may be selected from a plurality of profiles, such as the plurality of profiles 310. In some examples, method 400 selects a profile that is associated with the indicated clinical context. For example, each profile of a plurality of profiles may be associated with a different CID. Thus, for a given CID, method 400 selects the corresponding profile. In other examples, method 400 selects a profile that is associated with both the indicated clinical context and the selected scan protocol.

At 415, method 400 performs a scout scan. The scout scan may comprise a low-dose axial or helical scan of the patient. In some examples, the scout scan may be performed based on the selected scan protocol and/or the selected profile. For example, the selected scan protocol and/or the selected profile may prescribe a scan range, pitch, and dose settings for the scout scan. To perform the scout scan, the patient may be positioned within the imaging space of the imaging system. To that end, method 400 may control the table, such as table 228, via a table motor controller, such as table motor controller 226, to move such that the region of interest to be imaged is within the bore of the gantry. Method 400 then controls the imaging system to acquire scout data with a reduced radiation dosage with respect to a typical diagnostic scan. In some examples, method 400 may also control the table to move while acquiring scout data.

At 420, method 400 determines patient attributes. For example, method 400 may determine patient attributes, such as patient size, that may affect one or more acquisition settings. Method 400 may determine one or more patient attributes, such as patient size, based on the scout data acquired during the scout scan. Other patient attributes may not be determined from the scout scan. For example, patient attributes may include height, weight, age, and demographic information. Thus, in addition to or as an alternative to determining patient attributes from the scout scan, method 400 may receive one or more patient attributes from a user input, for example, via operator console 220. Further, method 400 may retrieve one or more patient attributes from an electronic medical record or another data source corresponding to the patient.

At 425, method 400 selects one or more sub-profiles based on the profile and the patient attributes. In particular, method 400 selects a plurality of sub-profiles, wherein each sub-profile of the selected plurality of sub-profiles is selected based on the profile, the patient attributes, or a combination of the profile and the patient attributes. The plurality of sub-profiles may include one or more of a radiation dose profile, an acquisition profile, a contrast profile, a reconstruction profile, and a reformat profile. Method 400 may select a radiation dose profile from a plurality of radiation dose profiles, an acquisition profile from a plurality of acquisition profiles, a contrast profile from a plurality of contrast profiles, a reconstruction profile from a plurality of reconstruction profiles, and a reformat profile from a plurality of reformat profiles.

As an illustrative and non-limiting example, method 400 may select a radiation dose profile, such as radiation dose profile 321, from a plurality of radiation dose profiles stored in a database, such as radiation dose profile database 320, based on a size of the patient and a profile. Further, the radiation dose profile may be selected from a subset of the plurality of radiation dose profiles. For example, the profile selected at 410 may include constraints on allowable radiation dose levels that excludes one or more radiation dose profiles of the plurality of radiation dose profiles from use during the scan. Thus, the radiation dose profile may be selected from at least a subset of radiation dose profiles based on one or more of the patient attributes (e.g., patient size) and the selected profile.

As another example, the profile selected at 410 may indicate a specific sub-profile from a plurality of sub-profiles. For example, a given profile 311 of a plurality of profiles 310 may be linked to a particular reformat profile 341 of a plurality of reformat profiles 341. Thus, method 400 may select one or more sub-profiles based solely on the profile selected at 410.

In some examples, method 400 may not select a particular type of sub-profile. For example, the profile selected at 410 may indicate that reformatted images are not necessary for the indicated clinical context, and so method 400 may not select a reformat profile from a plurality of reformat profiles. As another example, the selected scan profile and/or the indicated clinical context may indicate that contrast enhancement is not necessary for the scan, and thus method 400 may not select a contrast profile from a plurality of contrast profiles.

After selecting one or more sub-profiles, method 400 proceeds to 430. At 430, method 400 adjusts the scan protocol based on the profile and the sub-profiles. For example, the scan protocol prescribes the particular imaging settings for a scan and the subsequent image reconstruction. Method 400 may adjust the settings of the scan protocol to be in accordance with the settings prescribed by the profile selected at 410 and the one or more sub-profiles selected at 425. Additionally, in some examples, method 400 may optionally receive user input, for example via operator console 220, comprising instructions to adjust the scan protocol. In such examples, method 400 further adjusts the scan protocol based on the user input. For example, the profile and/or the one or more sub-profiles may prescribe a range of settings, and the user may select a particular setting within the prescribed range of settings.

Continuing at 435, method 400 performs a scan based on the adjusted scan protocol. In particular, method 400 controls the imaging system to scan the patient in accordance with the adjusted scan protocol to acquire projection data. After performing the scan and acquiring the projection data, method 400 continues to 440. At 440, method 400 reconstructs one or more images from the projection data acquired at 435 based on the sub-profiles. For example, method 400 may reconstruct one or more images from the projection data based on reconstruction settings prescribed by the reconstruction profile selected at 425. Method 400 may further reconstruct one or more images from the projection data according to reformat settings prescribed by the reformat profile selected at 425.

At 445, method 400 outputs the one or more images based on the sub-profiles. For example, method 400 outputs the one or more images reconstructed at 440 to one or more of a display such as display 232, a storage device such as mass storage 218, and a PACS such as PACS 224. The reconstruction profile and/or the reformat profile may include prescriptions for how or where the one or more images may be output. In such examples, method 400 outputs the one or more images in accordance with the prescriptions of the reconstruction profile and/or the reformat profile. Method 400 returns after outputting the one or more images.

Figure 5:
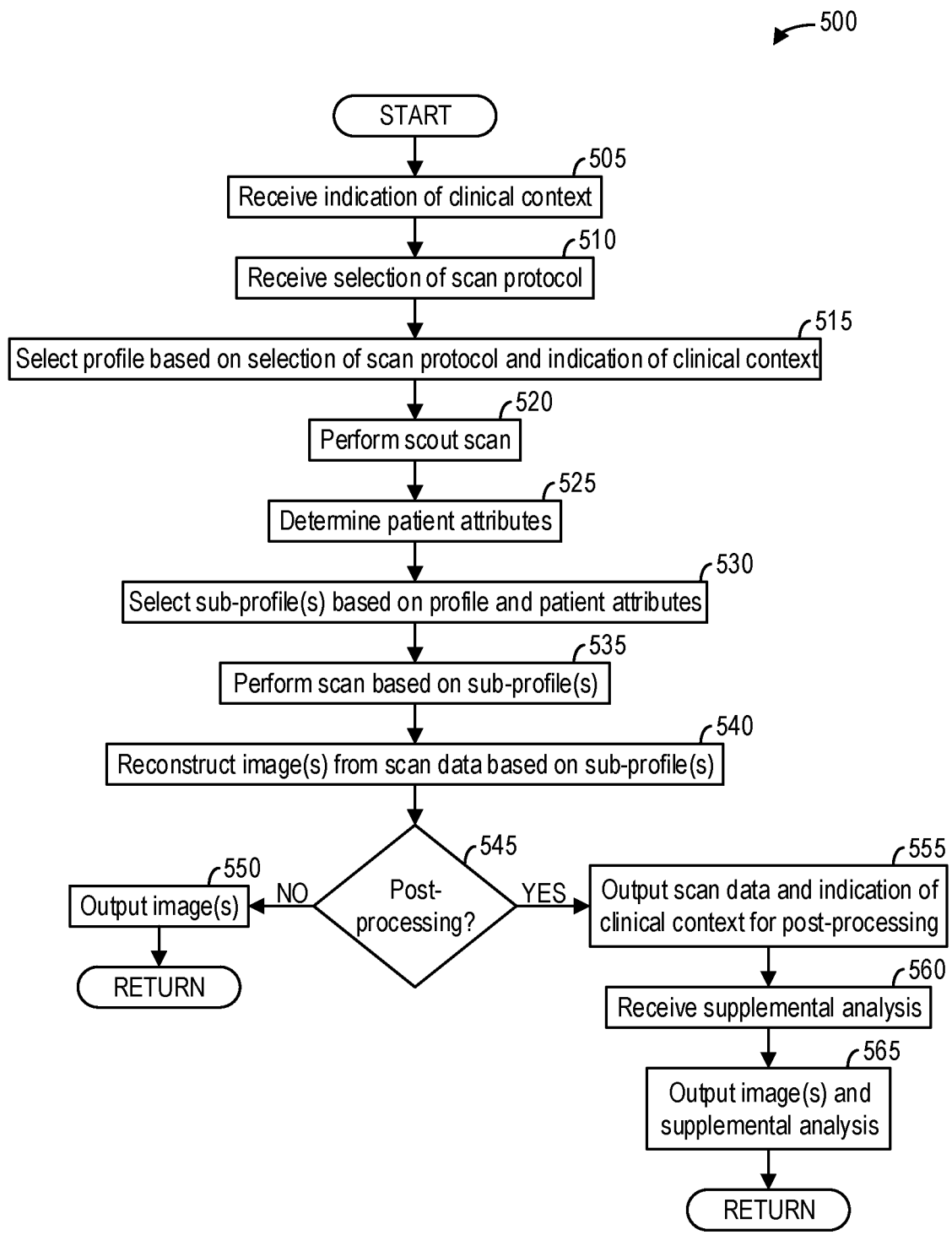
FIG. 5 shows a high-level flow chart illustrating another example method for profile-based scanning according to an embodiment.

FIG. 5 shows a high-level flow chart illustrating an example method 500 for profile-based scanning according to an embodiment. In particular, method 500 relates to a guided selection of imaging parameters for a given scan based on the clinical context of the scan. Method 500 is described with reference to the systems and components of FIGS. 1-3, though it should be understood that the method may be implemented with other systems and components without departing from the scope of the present disclosure. Method 500 may be implemented as executable instructions in non-transitory memory of a computing device, such as computing device 216.

Method 500 begins at 505. At 505, method 500 receives an indication of a clinical context. The indication of the clinical context may comprise a CID, for example. Method 500 may receive the indication of the clinical context from a user input, for example via an operator console 220. Alternatively, method 500 may retrieve, for example via PACS 224, the indication of the clinical context from an electronic medical record stored in an HIS or RIS.

At 510, method 500 receives a selection of a scan protocol. In some examples, the scan protocol may be selected based on user input. In such examples, method 500 receives the selection of the scan protocol from an operator console, such as operator console 220. In other examples, method 500 selects the scan protocol based on the indication of clinical context received at 505. For example, a CID received at 505 may be linked to a given scan protocol. In yet other examples, a CID received at 505 may be linked to two or more scan protocols which may be presented, for example via a user interface displayed on display 232, to a user who in turn selects, via operator console 220 for example, a desired scan protocol from the two or more scan protocols.

At 515, method 500 selects a profile based on the selection of the scan protocol and the indication of the clinical context. A plurality of profiles may include a profile for each combination of scan protocol and a clinical context, though it should be appreciated that some combinations of scan protocols and clinical contexts may share a single profile.

At 520, method 500 performs a scout scan. As discussed hereinabove with regard to FIG. 4, the scout scan may comprise a low-dose axial or helical scan of the patient. In some examples, the scout scan may be performed based on the selected scan protocol and/or the selected profile. For example, the selected scan protocol and/or the selected profile may prescribe a scan range, pitch, and dose settings for the scout scan. To perform the scout scan, the patient may be positioned within the imaging space of the imaging system. To that end, method 500 may control the table, such as table 228, via a table motor controller, such as table motor controller 226, to move such that the region of interest to be imaged is within the bore of the gantry. Method 500 then controls the imaging system to acquire scout data with a reduced radiation dosage with respect to a typical diagnostic scan. In some examples, method 500 may also control the table to move while acquiring scout data.

At 525, method 500 determines patient attributes. As discussed hereinabove with regard to FIG. 5, method 500 may determine patient attributes, such as patient size, that may affect one or more acquisition settings. Method 500 may determine one or more patient attributes, such as patient size, based on the scout data acquired during the scout scan. Other patient attributes may not be determined from the scout scan. For example, patient attributes may include height, weight, age, and demographic information. Thus, in addition to or as an alternative to determining patient attributes from the scout scan, method 500 may receive one or more patient attributes from a user input, for example, via operator console 220. Further, method 500 may retrieve, via PACS 224 for example, one or more patient attributes from an electronic medical record or another data source corresponding to the patient.

At 530, method 500 selects one or more sub-profiles based on the profile and the patient attributes. Similar to method 400, method 500 selects a plurality of sub-profiles, wherein each sub-profile of the selected plurality of sub-profiles is selected based on the profile, the patient attributes, or a combination of the profile and the patient attributes. The plurality of sub-profiles may include one or more of a radiation dose profile, an acquisition profile, a contrast profile, a reconstruction profile, and a reformat profile. Method 500 may select a radiation dose profile from a plurality of radiation dose profiles, an acquisition profile from a plurality of acquisition profiles, a contrast profile from a plurality of contrast profiles, a reconstruction profile from a plurality of reconstruction profiles, and a reformat profile from a plurality of reformat profiles.

As an illustrative and non-limiting example, method 500 may select a radiation dose profile, such as radiation dose profile 321, from a plurality of radiation dose profiles in a radiation dose profile database 320, based on a size of the patient and a profile. Further, the radiation dose profile may be selected from a subset of the plurality of radiation dose profiles. For example, the profile selected at 515 may include constraints on allowable kV levels that excludes one or more radiation dose profiles of the plurality of radiation dose profiles from use during the scan. Thus, the radiation dose profile may be selected from at least a subset of radiation dose profiles based on one or more of the patient attributes (e.g., patient size) and the selected profile.

As another example, method 500 may select a contrast profile, such as contrast profile 331, from a plurality of contrast profiles, such as the plurality of contrast profiles 330, based on a size of the patient, an age of the patient, and the profile selected at 515. As an illustrative example, younger patients may be prescribed more contrast whereas older patients may be prescribed less contrast. The particular amount of contrast prescribed for a given patient may be specified based on a combination of the size and the age of the patient. Furthermore, the profile may include target image quality metrics for the clinical context, and so the contrast profile may be selected such that an appropriate amount of contrast is used to achieve the target image quality metrics.

As another example, the profile selected at 515 may indicate a specific sub-profile from a plurality of sub-profiles. For example, a given profile 311 of a plurality of profiles 310 may be linked to a particular reformat profile 341 of a plurality of reformat profiles 341. Thus, method 500 may select one or more sub-profiles based solely on the profile selected at 515.

In some examples, method 500 may not select a particular type of sub-profile. For example, the profile selected at 515 may indicate that reformatted images are not necessary for the indicated clinical context, and so method 500 may not select a reformat profile from a plurality of reformat profiles. As another example, the selected scan profile and/or the indicated clinical context may indicate that contrast enhancement is not necessary for the scan, and thus method 500 may not select a contrast profile from a plurality of contrast profiles.

After selecting the sub-profiles, method 500 continues to 535. At 535, method 500 performs a scan based on the sub-profiles. In particular, method 500 performs the scan in accordance with the imaging settings prescribed by the profile and the one or more sub-profiles. For example, the scan may be performed according to kV settings prescribed by the selected kV profile and acquisition settings (e.g., mA, filters, and so on) prescribed by the selected acquisition profile.

At 540, method 500 reconstructs images from scan data based on the sub-profiles. For example, method 500 may reconstruct one or more images from the projection data based on reconstruction settings prescribed by the reconstruction profile selected at 530. Method 500 may further reconstruct one or more images from the projection data according to reformat settings prescribed by the reformat profile selected at 530.

Continuing at 545, method 500 determines if the indication of clinical context is linked to a post-processing method or methods. For example, one or more of the indication of clinical context received at 505, the profile selected at 515, and one or more of the sub-profiles selected at 530 may indicate that one or more post-processing methods should be applied to the projection data (also referred to herein as scan data) acquired at 535.

If the indication of clinical context is not linked to a post-processing method or methods ("NO"), method 500 proceeds to 550. At 550, method 500 outputs the image(s) reconstructed at 540. The one or more images may be output to one or more of a display such as display 232, a storage device such as mass storage 218, and a PACS such as PACS 224. Method 500 then returns.

However, referring again to 545, if the indication of clinical context is linked to a post-processing method ("YES"), method 500 proceeds to 555. At 555, method 500 outputs the scan data and the indication of clinical context for post-processing. For example, method 500 may output the scan data and the indication of clinical context to a PACS such as PACS 224, wherein the scan data is post-processed based on the indication of the clinical context. Outputting the scan data and the indication of clinical context may include attaching an image-based CID corresponding to the indicated clinical context to one or more of the reconstructed images and/or the projection data. The post-processing may include, as illustrative and non-limiting examples, artifact reduction algorithms that correct the scan data to reduce image artifacts, segmentation algorithms that selectively partition portions of an image volume, and deep learning algorithms that provide automated analysis of the scan data and/or images reconstructed from the scan data. In some examples, method 500 may output the scan data and the indication of clinical context to a local computing device, such as computing device 216 and/or image reconstructor 230, for the post-processing. At 560, method 500 receives a supplemental analysis comprising the results of the post-processing. Continuing at 565, method 500 outputs the images and the supplemental analysis, for example to one or more of a display such as display 232, a storage device such as mass storage 218, or a PACS such as PACS 224. Method 500 then returns.

Thus, method 500 may use the indication of clinical context received at 505 to automatically trigger downstream post-processing. It should be appreciated that while the post-processing steps 545, 555, and 560 are depicted as occurring after an image is reconstructed at 540, the post-processing steps 545, 555, and 560 may occur in parallel with the scan at 535 and/or the image reconstruction at 540. For example, if the profile selected at 515 and/or one or more of the sub-profiles selected at 530 indicate that post-processing is desired, method 500 may output the scan data along with the indication of clinical context while the scan is being performed so that the total amount of time for imaging and post-processing may be reduced.

A technical effect of the disclosure is the automated guidance for a clinical context on the varied and complex trade-offs necessary to ensure reliable diagnostic outcomes with consistent image quality across patients. Another technical effect of the disclosure is a patient-specific selection of acquisition settings to define a scan prescription more efficiently while improving quality assurance and managing an x-ray radiation dose of the patient. Another technical effect of the disclosure is the automatic execution of downstream post-processing techniques for a given clinical context.

In one embodiment, a method comprises selecting a profile based on an indication of clinical context for a scan of a patient, selecting one or more sub-profiles based on the profile, selecting imaging settings for the scan based on the profile and the one or more sub-profiles, and performing the scan according to the selected imaging settings.

In a first example of the method, the method further comprises receiving the indication of clinical context via an operator console. In a second example of the method optionally including the first example, selecting the profile based on the indication of clinical context comprises retrieving the profile from a profile database containing a plurality of profiles, wherein the profile is associated with the indicated clinical context and wherein the profile designates prioritization of imaging settings to achieve one or more of an image quality target and a dose target. In a third example of the method optionally including one or more of the first and second examples, the profile is linked to a plurality of sub-profiles, and selecting the one or more sub-profiles based on the profile comprises selecting one of the plurality of sub-profiles based on patient attributes of the patient. In a fourth example of the method optionally including one or more of the first through third examples, the patient attributes include one or more of a patient size, heart rate, and age of the patient, and the method further comprises determining the patient size from scout data acquired during a scout scan of the patient. In a fifth example of the method optionally including one or more of the first through fourth examples, the method further comprises receiving one or more of an indication of the image quality target and an indication of the dose target via an operator console. In a sixth example of the method optionally including one or more of the first through fifth examples, the one or more sub-profiles include a prescription of one or more of radiation dose parameters, acquisition parameters, contrast parameters, reconstruction parameters, and reformat parameters. In a seventh example of the method optionally including one or more of the first through sixth examples, selecting the imaging settings for the scan based on the profile and the one or more sub-profiles comprises selecting the imaging settings according to the prescription of the one or more sub-profiles. In an eighth example of the method optionally including one or more of the first through seventh examples, the method further comprises reconstructing an image based on the one or more sub-profiles, wherein the one or more sub-profiles prescribes one or more of a reconstruction kernel, slice thickness, and temporal window. In a ninth example of the method optionally including one or more of the first through eighth examples, the method further comprises automatically outputting the image and the indication of clinical context for post-processing responsive to the profile prescribing the post-processing.

In another embodiment, a method comprises receiving an indication of clinical context for a scan of a patient, selecting a profile associated with the indication of clinical context, determining one or more patient attributes, selecting one or more sub-profiles associated with the profile based on the one or more patient attributes, performing the scan of the patient according to acquisition settings prescribed by the one or more sub-profiles, and reconstructing an image from projection data acquired during the scan according to reconstruction settings prescribed by the one or more sub-profiles.

In a first example of the method, receiving the indication of clinical context comprises receiving a selection of a scan protocol for the scan, the scan protocol including the indication of clinical context. In a second example of the method optionally including the first example, the method further comprises performing a scout scan of the patient, wherein determining the one or more patient attributes comprises determining a size of the patient based on the scout scan. In a third example of the method optionally including one or more of the first and second examples, the acquisition settings prescribed by the one or more sub-profiles include one or more of tube voltage, tube current, bowtie filter, gantry rotation speed, focal spot size, scan range, table pitch, helical pitch, and collimation, and the reconstruction settings include one or more of a reconstruction kernel, post-processing filters, slice thickness, and temporal window. In a fourth example of the method optionally including one or more of the first through third examples, the method further comprises generating a reformatted image from the projection data according to reformat settings prescribed by the one or more sub-profiles.

In yet another embodiment, a system comprises an x-ray source that emits a beam of x-rays towards a subject to be imaged, a detector that receives the x-rays attenuated by the subject, a data acquisition system (DAS) operably connected to the detector, and a computing device operably connected to the DAS and configured with executable instructions in non-transitory memory that when executed cause the computing device to: select a profile based on an indication of clinical context for a scan of the subject; select one or more sub-profiles based on the profile and attributes of the subject; select imaging settings for the scan based on the profile and the one or more sub-profiles; and perform the scan with the x-ray source and the detector according to the selected imaging settings.

In a first example of the system, selecting the profile based on the indication of clinical context comprises retrieving the profile from a profile database containing a plurality of profiles, wherein the profile is associated with the indicated clinical context and wherein the profile designates prioritization of imaging settings to achieve one or more of an image quality target and a dose target. In a second example of the system optionally including the first example, the system further comprises an operator console communicatively coupled to the computing device, wherein the computing device is configured with executable instructions in non-transitory memory that when executed cause the computing device to receive, via the operator console, one or more of the indication of clinical context, the image quality target, and the dose target. In a third example of the system optionally including one or more of the first and second examples, the one or more sub-profiles include a prescription of one or more of radiation dose parameters, acquisition parameters, contrast parameters, reconstruction parameters, and reformat parameters, and wherein selecting the imaging settings for the scan based on the profile and the one or more sub-profiles comprises selecting the imaging settings according to the prescription. In a fourth example of the system optionally including one or more of the first through third examples, the system further comprises a display communicatively coupled to the computing device, wherein the computing device is configured with executable instructions in non-transitory memory that when executed cause the computing device to reconstruct, based on the reconstruction parameters prescribed by the one or more sub-profiles, an image from projection data acquired during the scan, and output the image to the display.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method comprising:
    selecting a profile based on an indication of clinical context for a scan of a patient;
    automatically retrieving one or more sub-profiles linked to the profile, including a sub-profile from each of a plurality of radiation dose profiles, a plurality of acquisition profiles, a plurality of contrast profiles, a plurality of reconstruction profiles, and a plurality of reformat profiles, wherein each sub-profile includes at least one scan setting that relates to the sub-profile;
    selecting imaging settings for the scan based on the profile and the one or more sub-profiles; and
    performing the scan according to the selected imaging settings.

2. The method of claim 1, further comprising receiving the indication of the clinical context via an operator console.

3. The method of claim 1, wherein selecting the profile based on the indication of the clinical context comprises automatically retrieving the profile from a profile database containing a plurality of profiles, wherein the profile is associated with the clinical context and wherein the profile designates prioritization of imaging settings to achieve one or more of an image quality target and a dose target.

4. The method of claim 3, wherein automatically retrieving the one or more sub-profiles linked to the profile comprises automatically retrieving one of the plurality of sub-profiles from a corresponding sub-profile database of a plurality of sub-profile databases based on patient attributes of the patient.

5. The method of claim 4, wherein the patient attributes include one or more of a patient size, heart rate, and age of the patient, and further comprising performing a scout scan of the patient based on the profile, and determining the patient size from scout data acquired during the scout scan of the patient.

6. The method of claim 3, further comprising receiving one or more of an indication of the image quality target and an indication of the dose target via an operator console, wherein selecting the one or more sub-profiles based on the profile further comprises selecting, from a subset of sub-profiles in a plurality of sub-profiles stored in a sub-profile database, the one or more sub-profiles based on the one or more of the indication of the image quality target and the indication of the dose target, the subset of sub-profiles linked to the profile.

7. The method of claim 1, wherein the one or more sub-profiles include a prescription of one or more of radiation dose parameters, acquisition parameters, contrast parameters, reconstruction parameters, and reformat parameters.

8. The method of claim 7, wherein selecting the imaging settings for the scan based on the profile and the one or more sub-profiles comprises selecting the imaging settings according to the prescription of the one or more sub-profiles.

9. The method of claim 1, further comprising reconstructing an image based on the one or more sub-profiles, wherein the one or more sub-profiles prescribes one or more of a reconstruction kernel, slice thickness, and temporal window.

10. The method of claim 9, further comprising automatically outputting the image and the indication of the clinical context for post-processing responsive to the profile prescribing the post-processing.

11. A method, comprising:
receiving an indication of clinical context for a scan of a patient;
selecting a profile associated with the indication of the clinical context;
determining one or more patient attributes;
automatically retrieving one or more sub-profiles linked to the profile, from a plurality of sub-profiles in a sub-profile database, based on the one or more patient attributes, wherein each sub-profile includes at least one scan setting that relates to the sub-profile;
performing the scan of the patient according to acquisition settings prescribed by the one or more sub-profiles; and
reconstructing an image from projection data acquired during the scan according to reconstruction settings prescribed by the one or more sub-profiles.

12. The method of claim 11, further comprising:
receiving a scan protocol; and
selecting the profile based on the scan protocol.

13. The method of claim 11, further comprising performing a scout scan of the patient, wherein determining the one or more patient attributes comprises determining a size of the patient based on the scout scan.

14. The method of claim 11, wherein the acquisition settings prescribed by the one or more sub-profiles includes one or more of tube voltage, tube current, bowtie filter, gantry rotation speed, focal spot size, scan range, table pitch, helical pitch, and collimation, wherein the reconstruction settings include one or more of a reconstruction kernel, post-processing filters, slice thickness, and temporal window.

15. The method of claim 11, further comprising generating a reformatted image from the projection data according to reformat settings prescribed by the one or more sub-profiles.

16. A system, comprising:
an x-ray source that emits a beam of x-rays towards a subject to be imaged;
a detector that receives the x-rays attenuated by the subject;
a data acquisition system (DAS) operably connected to the detector; and
a computing device operably connected to the DAS and configured with executable instructions in non-transitory memory that when executed cause the computing device to:
select a profile, from a plurality of profiles in a profile database, based on an indication of clinical context for a scan of the subject;
automatically retrieve one or more sub-profiles linked to the profile, from a plurality of sub-profiles in at least one sub-profile database, based on the profile and attributes of the subject, including a sub-profile from each of a plurality of radiation dose profiles, a plurality of acquisition profiles, a plurality of contrast profiles, a plurality of reconstruction profiles, and a plurality of reformat profiles, wherein each sub-profile includes at least one scan setting that relates to the sub-profile;
select imaging settings for the scan based on the profile and the one or more sub-profiles; and
perform the scan with the x-ray source and the detector according to the selected imaging settings.

17. The system of claim 16, wherein selecting the profile based on the indication of the clinical context comprises retrieving the profile from a profile database containing a plurality of profiles, wherein the profile is associated with the clinical context and wherein the profile designates prioritization of imaging settings to achieve one or more of an image quality target and a dose target.

18. The system of claim 17, further comprising an operator console communicatively coupled to the computing device, wherein the computing device is configured with executable instructions in non-transitory memory that when executed cause the computing device to receive, via the operator console, one or more of the indication of the clinical context, the image quality target, and the dose target.

19. The system of claim 18, wherein the one or more sub-profiles include a prescription of one or more of radiation dose parameters, acquisition parameters, contrast parameters, reconstruction parameters, and reformat parameters, and wherein selecting the imaging settings for the scan based on the profile and the one or more sub-profiles comprises selecting the imaging settings according to the prescription.

20. The system of claim 18, further comprising a display communicatively coupled to the computing device, wherein the computing device is configured with executable instructions in non-transitory memory that when executed cause the computing device to reconstruct, based on the reconstruction parameters prescribed by the one or more sub-profiles, an image from projection data acquired during the scan, and output the image to the display.

* * * * *